(12) United States Patent
Aziz

(10) Patent No.: US 7,051,594 B1
(45) Date of Patent: May 30, 2006

(54) PRESSURE GAUGE AND MEDICAL APPARATUS WITH SAME

(76) Inventor: Mohamed Fazni Aziz, 3930 Fox Chase Run, Bloomington, IN (US) 47401

( * ) Notice: Subject to any disclaimer, the term of this patent is extended or adjusted under 35 U.S.C. 154(b) by 64 days.

(21) Appl. No.: 10/990,867

(22) Filed: Nov. 17, 2004

(51) Int. Cl.
*G01L 7/00* (2006.01)

(52) U.S. Cl. .......................................... 73/700; 600/587

(58) Field of Classification Search ................... 73/700
See application file for complete search history.

(56) References Cited

U.S. PATENT DOCUMENTS

| | | | |
|---|---|---|---|
| 2,770,134 A | * | 11/1956 | Galperin .................... 73/146.8 |
| 3,191,440 A | * | 6/1965 | Miller .......................... 73/705 |
| 3,249,760 A | * | 5/1966 | Miller .................... 250/231.19 |
| 3,555,882 A | | 1/1971 | Robinson |
| 3,604,680 A | | 9/1971 | Kay et al. |
| 3,726,142 A | | 4/1973 | Ashton |
| 4,387,600 A | | 6/1983 | Kranz |
| 4,785,821 A | | 11/1988 | Udell et al. |
| 4,872,483 A | | 10/1989 | Shah |
| 4,967,600 A | | 11/1990 | Keller |
| 4,995,264 A | | 2/1991 | Stocker et al. |
| 5,021,046 A | | 6/1991 | Wallace |
| 5,138,886 A | | 8/1992 | Tilley, Sr. |
| 5,189,917 A | | 3/1993 | Vijayakumar et al. |
| 5,449,344 A | | 9/1995 | Taylor |
| 5,557,049 A | | 9/1996 | Ratner |
| 6,382,031 B1 | | 5/2002 | Mast et al. |
| 6,510,741 B1 | | 1/2003 | Condrea et al. |

\* cited by examiner

*Primary Examiner*—Edward Lefkowitz
*Assistant Examiner*—Andre Allen
(74) *Attorney, Agent, or Firm*—Liell & McNeil

(57) ABSTRACT

Pressure gauges used to indicate the pressure of the air being supplied to a patient during resuscitation should be able to indicate the pressure quickly and simply. In the present disclosure, a medical apparatus includes an apparatus body defining a fluid cavity that is fluidly connected to an expandable pressure chamber of a pressure gauge. The pressure chamber, a battery and at least one pressure indicator are, at least partially, positioned within a gauge body of the pressure gauge. An electrical conductor is moveable with the expandable pressure chamber among a plurality of positions and with respect to the gauge body. When the electrical conductor is in a first position, the battery is out of electrical connection with the at least one pressure indicator. When in the second position, the electrical conductor electrically connects the battery with the at least one pressure indicator.

20 Claims, 8 Drawing Sheets

PRESSURE GAUGE AND MEDICAL APPARATUS WITH SAME

TECHNICAL FIELD

The present disclosure relates generally to pressure gauges, and more specifically to medical apparatuses using pressure gauges to indicate fluid pressure within a fluid cavity of the medical apparatus.

BACKGROUND

Pressure gauges, often referred to as manometers, that monitor the pressure of a gas or fluid are often used in fast-paced, emergency medical situations. For instance, manometers, such as the manometer described in U.S. Pat. No. 5,557,049, issued to Ratner, on Sep. 17, 1996, are coupled to medical apparatuses, such a resuscitation bags, used in cardiopulmonary resuscitation (CPR) in order to monitor the air pressure being supplied to a patient who is being resuscitated. The manometer is fluidly connected to a fluid cavity within the resuscitation bag through which the supply of air passes before being delivered to a mask placed over the patient's mouth and nose. A CPR technician can monitor the pressure within the fluid cavity by viewing a pressure indicator of the manometer. The pressure indicator includes a pointer that is rotatably disposed with respect to a dial with sequentially arranged pressure values. The pointer is coupled to move with a diaphragm that moves with the air entering a pressure chamber of the manometer from the fluid cavity. Thus, the position of the pointer with respect to the dial will indicate the pressure of the air within the fluid cavity that will be supplied to the patient.

Although the CPR technician can monitor the air pressure being supplied to the patient via the Ratner manometer, the technician must divert a significant amount of her attention from the patient to the manometer in order to read the pressure indicator. The technician must take the time to observe the pointer's location in relation to numerical pressure values within the dial. In emergency situations in which a patient is being resuscitated, any attention diverted away from the patient can reduce the patient's chance of successful treatment.

Moreover, many manometers used with medial apparatuses, such as resuscitation bags, are prone to leakage. Leakage of the air from the manometer can cause the pressure indicator to fluctuate, making it difficult for the technician to determine the actual pressure of the air being delivered to the patient.

The present disclosure is directed at overcoming one or more of the problems set forth above.

SUMMARY OF INVENTION

According to one aspect of the present disclosure, a pressure gauge includes a gauge body in which at least one electrically actuated pressure indicator, at least one battery, and an expandable pressure chamber with a fluid inlet port are at least partially positioned. An electrical conductor is moveable among a plurality of positions with the expandable pressure chamber and with respect to the gauge body. When the electrical conductor is in a first position, the battery is out of electrical connection with the at least one pressure indicator. When the electrical conductor is in a second position, the electrical conductor electrically connects the battery with the at least one pressure indicator.

According to another aspect of the present disclosure, a medical apparatus includes an apparatus body that defines a fluid cavity. A pressure gauge is fluidly connected to the fluid cavity of the medical apparatus via a fluid inlet port of a pressure chamber at least partially positioned within a gauge body. At least one battery and at least one electrically actuated pressure indicator are at least partially positioned within the gauge body. An electrical conductor is moveable among a plurality of positions with the expandable pressure chamber and with respect to the gauge body. When the electrical conductor is in a first position, the battery is out of electrical connection with the at least one pressure indicator. When the electrical conductor is in a second position, the electrical conductor electrically connects the battery with the at least one pressure indicator.

According to yet another aspect of the present disclosure, fluid pressure within a fluid cavity is indicated by fluidly connecting the fluid cavity with a fluid inlet port of an expandable pressure chamber so that the pressure chamber is expanded with the fluid pressure within the fluid cavity. An electrical conductor is moved with the expanding pressure chamber and electrically connects a battery with a plurality of pressure indicators when the expandable pressure chamber is at a predetermined position.

BRIEF DESCRIPTION OF THE DRAWINGS

FIG. 1a is a diagrammatic isometric view of a medical apparatus including a pressure gauge, according to a preferred version of the present disclosure;

FIG. 1b is a sectioned top diagrammatic view of a the medical apparatus of FIG. 1a;

FIG. 2a is a top diagrammatic view of an internal structure of the pressure gauge within FIGS. 1a and 1b;

FIG. 2b is a side diagrammatic view of the internal structure of the pressure gauge of FIG. 2a;

FIG. 2c is an isometric view of the pressure gauge of FIG. 2a;

FIG. 3a is an isometric view of a pressure gauge, according to a first alternative embodiment;

FIG. 3b is an exploded view of the pressure gauge of FIG. 3a;

FIG. 3c is a side diagrammatic view of an internal structure of the pressure gauge of FIG. 3a;

FIG. 4b is a bottom diagrammatic view of the internal structure of the pressure gauge in FIG. 4a;

DETAILED DESCRIPTION

Figures 1A, 1B:
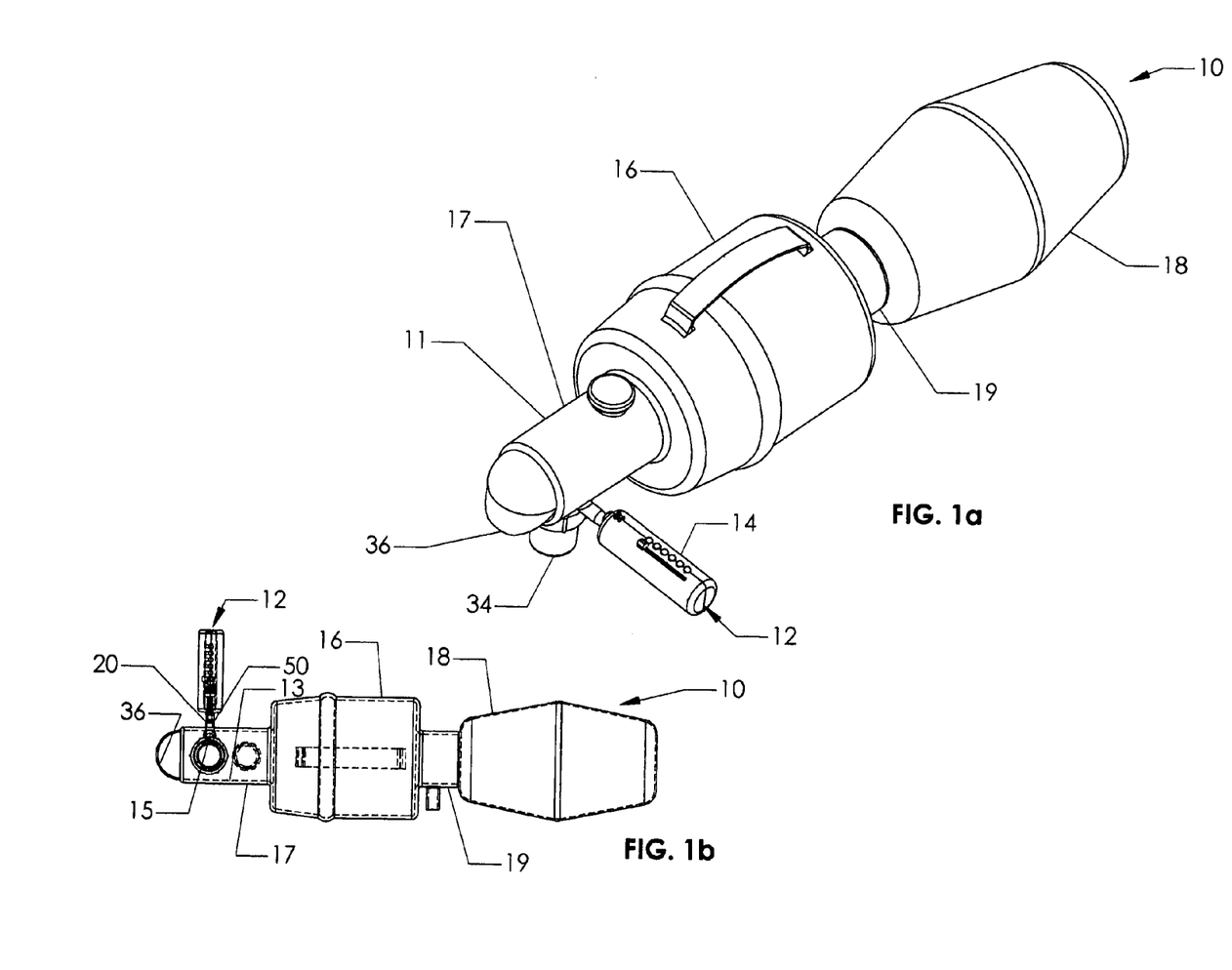

Referring to FIG. 1, there is shown a diagrammatic representation of a medical apparatus including a pressure gauge 12, according to the present disclosure. Although the medical apparatus is illustrated as a cardiopulmonary resuscitator (CPR) bag assembly 10, it should be appreciated that the medical apparatus could include various types of medical apparatuses that supply fluid, being air or liquid, to a patient, including, but not limited to, a breathing tube or hyperinflation system. Further, it should be appreciated that the present disclosure contemplates use with apparatuses other than medical apparatuses. For instance, the present disclosure could be used to monitor the pressure within a firefighter's or deep sea diver's oxygen tank.

The CPR bag assembly 10 includes an apparatus body 11 that includes a squeeze bulb 16 positioned between a reservoir bag 18 and an outlet assembly 17. The reservoir bag 18 is fluidly connected to a supply of oxygen (not shown) and defines a cavity for oxygen accumulation during resuscitation. It should be appreciated that the squeeze bulb 16 could be fluidly connected to the supply of oxygen without the use of the reservoir bag 18. The squeeze bulb 16 includes an oxygen inlet port 19 in which an inlet check valve is positioned and through which the oxygen can be drawn into the squeeze bulb 16. When the squeeze bulb 16 is compressed, the inlet check valve of the bulb 16 is closed and an outlet check valve is opened, allowing oxygen to flow from the bulb 16 to the outlet assembly 17. When the squeeze bulb 16 is released, the inlet check valve opens and the outlet check valve closes allowing fresh oxygen to fill the squeeze bulb 16. The oxygen can flow through the outlet assembly 17, past an outlet valve (not shown) and through an outlet 34 defined by the outlet assembly 17 to a breathing mask (not shown) placed over a patient's mouth and nose. When the patient exhales, the exhaled air can flow back into the outlet assembly 17 via the outlet 34 and, due to the pressure of the air, close the outlet valve and open a ventilation port 36. Thus, as known in the art, the CPR bag assembly 10 both supplies oxygen to the patient and exhausts carbon dioxide coming from the patient. Although the present disclosure can operate with any type of valve or valves used to supply and vent air from the patient, it is known in the art to utilize a duckbill-type check valve that can operate as both the outlet valve and the ventilation valve. A pressure gauge 12 is attached to the apparatus body 11 of the CPR bag assembly 10. The pressure gauge 12 is preferably a manometer that indicates the pressure of the oxygen being provided to the patient.

Referring to FIG. 1b, there is shown a sectioned top diagrammatic representation of the CPR bag assembly 10 of FIG. 1. The outlet assembly 17 defines a fluid chamber 13 that extends between the outlet of the squeeze bulb 16 and the outlet valve. The pressure within the fluid cavity 13 opens the outlet valve so the oxygen can be delivered to the patient. Thus, the pressure within the fluid cavity 13 is the pressure of the oxygen being supplied to the patient. The pressure gauge 12 is attached to the apparatus body 11 such that the fluid chamber 13 is fluidly connected to a fluid inlet port 15 of an expandable pressure chamber 20 partially positioned within a gauge body 14. The pressure gauge 12 can indicate the pressure of the oxygen acting to open the outlet valve and that will be supplied to the patient through the outlet valve. Although the pressure gauge 12 can be attached to the apparatus body 11 by various methods, the pressure gauge 12 is preferably removeably attached to the apparatus body 11 by inserting an attachment portion 50 of the pressure chamber 20 extending outside of the gauge body 14 into an attachment bore defined by the outlet assembly 17. The attachment portion 50 and the attachment bore will be sized such that the gauge 12 can be securely attached to the CPR bag assembly 17, but detached with force applied by a technician.

Figures 2A, 2B, 2C:
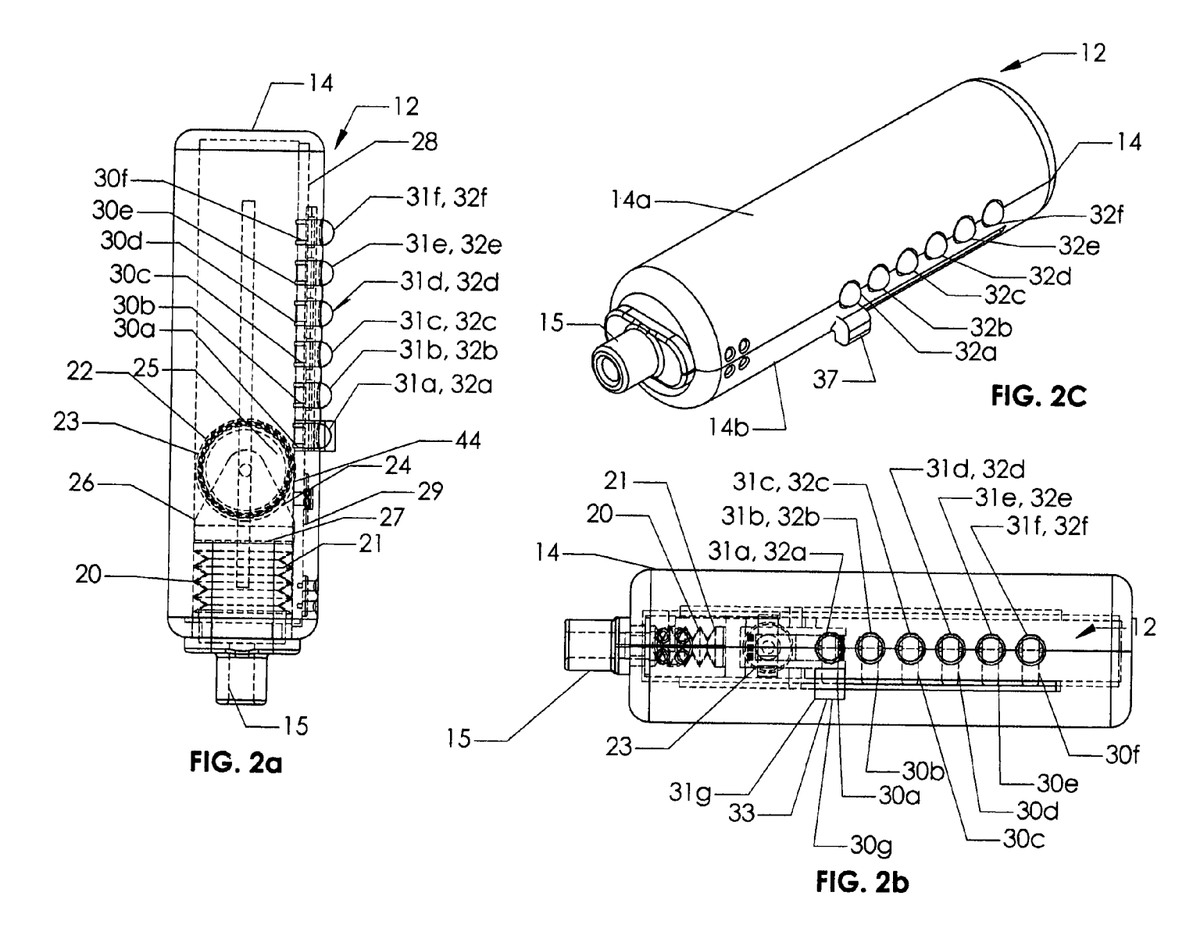

Referring to FIG. 2a, there is shown a sectioned top diagrammatic representation of an internal structure of the pressure gauge 12. The expandable pressure chamber 20 is defined, in part, by bellows-type walls 21 and is expandable among a plurality of predetermined positions. Although the expandable pressure chamber 20 is illustrated as a bellows-type chamber, it should be appreciated that the expandable pressure chamber 20 could be any type of chamber that expands with pressure, including, but not limited to, a balloon-type chamber. Each predetermined position corresponds to a known pressure within the expandable pressure chamber 20. For instance, in the illustrated example, when the pressure chamber 20 is in a first predetermined position as shown in FIG. 1a, there is less than 10 hPa of pressure within the pressure chamber 20. When the pressure chamber 20 is in a second predetermined position, there is approximately 20 hPa within the pressure chamber 20. Although the present disclosure contemplates the pressure chamber including any number of predetermined positions, the pressure chamber 20 must include at least two predetermined positions. In the illustrated embodiment, the pressure chamber 20 includes seven predetermined positions. A third, fourth, fifth, sixth and seventh predetermined positions correspond to 30 hPa, 40 hPa, 50 hPa, and 60 hPa, respectively. Those skilled in the art will appreciate that the pressure gauge can be designed such that the predetermined positions correspond to any pressure at which it is desirable for the pressure gauge to indicate.

An electrical conductor 22 is moveable with the expandable pressure chamber 20 among a plurality of positions and with respect to the gauge body 14. Although not necessary, the electrical conductor 22 preferably includes an electrically conductive spring that is coupled to move with the expandable pressure chamber 20. In the embodiment illustrated in FIG. 2, the electrical conductor 22 is a coil-band spring 23 coiled around a spring slide assembly 24. The spring slide assembly 24 includes a spring holder 25 that is rotatably attached to a spring slide 26 that includes a chamber contact surface 27. The spring slide assembly 24 can slide along the gauge body 14 in a conventional manner. A first end 44 of the spring 23, is attached to a gauge component such that when the spring 23, via the spring slide assembly 24, moves with the expandable pressure chamber 20, the coil-band spring 23 will uncoil along a spring path. Although, in the illustrated embodiment, the first end 44 is screwed to the gauge component, being a circuit board 28, it should be appreciated that one end of the spring could be secured to various gauge components, including the gauge housing, by various means. In the illustrated embodiment, the screw is also in contact with the battery 29, and thus, provides as an electrical connection between a battery 29 and the spring 23.

The electric circuit board 28 preferably includes, at least, six parallel electric circuits 30a–f, each including a pressure indicator 31a–f. It should be appreciated that the present disclosure contemplates the circuit board 28 having any number of electric circuits, including only one. All of the parallel electric circuit 30a–f include the battery 29, preferably a small, button-type battery. The pressure indicator 31a–f within each circuit 30a–f and the coil-band spring 23 are electrically connected to opposite poles of the battery 29. A resister (not shown) is preferably positioned within the connection between the battery 29 and each pressure indicator 31a–f. Those skilled in the art will appreciate that the resisters can conserve the power of the battery 29, thereby increasing the life of the pressure gauge 12. A lead (not shown) extends from each pressure indicator 31a–f and is exposed and positioned within the spring path. For purposes of this discussion, the lead is the point at which each circuit is broken. Thus, each electric circuit 30a–f is an open electric circuit until the coil-band spring 23 makes contact with the lead for each electric circuit 30a–f. Those skilled in the art will appreciate that the present disclosure contemplates various ways of wiring the circuits such that the circuits can be closed by the movement of the spring 23. Moreover, the present disclosure contemplates the electric circuits being wired differently from one another.

Although the present disclosure contemplates any number and various types of electrically-actuated pressure indicators, the six pressure indicators 31a–f included within the six electric circuits 30a–f are preferably light emitting diodes 32a–f. For instance, the pressure indicators could include a LCD display or conventional light bulbs. When the expandable pressure chamber 20 is in the first predetermined position, the coil-band spring 23 is in a first position (as shown in FIG. 2) in which the coil-band spring 23 is out of contact with the electrical circuits 30a–f. The battery 29 is out of electrical connection with all of the light emitting diodes 31a–f. When the expandable pressure chamber 20 is in the second predetermined position, the coil-band spring 23 is in a second position in which the coil-band spring 23 is in contact with the first electrical circuit 30a and electrically connecting the battery 29 with the first light emitting diode 31a. When the expandable pressure chamber 20 is in the third predetermined position, the coil-band spring 23 is in a third position in which the coil-band spring 23 is in contact with the first and second electrical circuits 30a and 30b and electrically connecting the battery 29 with the first and second light emitting diodes 31a and 31b. When the expandable pressure chamber 20 is in the fourth predetermined position, the coil-band spring 23 is in a fourth position in which the coil-band spring 23 is in contact with the first, second and third electrical circuits 30a, 30b and 30c and electrically connecting the battery 29 with the first, second and third light emitting diodes 31a–c. When the expandable pressure chamber 20 is in the fifth predetermined position, the coil-band spring 23 is in a fifth position in which the spring 23 is in contact with the first, second, third and fourth electric circuits 30a–d and electrically connecting the battery 29 with the first, second, third and fourth light emitting diodes 33a–d. When the expandable pressure chamber 20 is in the sixth predetermined position, the coil-band spring 23 is in a sixth position, in which the spring 23 is in contact with the first, second, third, fourth, and fifth electrical circuits 30a–e and electrically connecting the battery 29 with the first, second, third, fourth and fifth light emitting diodes 33a–e. When the expandable pressure chamber 20 is in the seventh predetermined positions, the coil-band spring 23 is in a seventh position, in which the spring 23 is in contact with the first, second, third, fourth, fifth and sixth electric circuits 30a–f and electrically connecting the battery 29 with the first, second, third, fourth, fifth and sixth light emitting diodes 33a–f.

Referring to FIG. 2b, there is shown a side diagrammatic representation of the internal structure of the pressure gauge 12. The plurality of pressure indicators 31 also includes a seventh pressure indicator 31g, being a sound emitting device 33, illustrated as an audible cue. The present disclosure contemplates the pressure gauge 12 including only one pressure indicator. For instance, the pressure indicator could include one sound emitting device or one light emitting diode that sounds or illuminates when a threshold pressure is reached. In addition, the present disclosure contemplates one light emitting diode that changes colors or intensity as the pressure reaches different predetermined pressures, or one sound emitting device that changes pitch as the pressure reaches different predetermined pressures. The sound emitting device 33 is also positioned within an electric circuit 30g. The sound emitting device 33 is wired to the battery 29 similar to the light emitting diodes 32a–f. Thus, when the coil-band spring 23 comes in contact with the lead extending from the sound emitting device 33, the sound emitting device 33 is in electrical connection with the battery 29. Unlike the light emitting diodes 32a–f, the sound emitting device 33 is adjustable among a plurality of positions, each position corresponding to a position of a light emitting diode 31a–f.

Figures 3A, 3B:
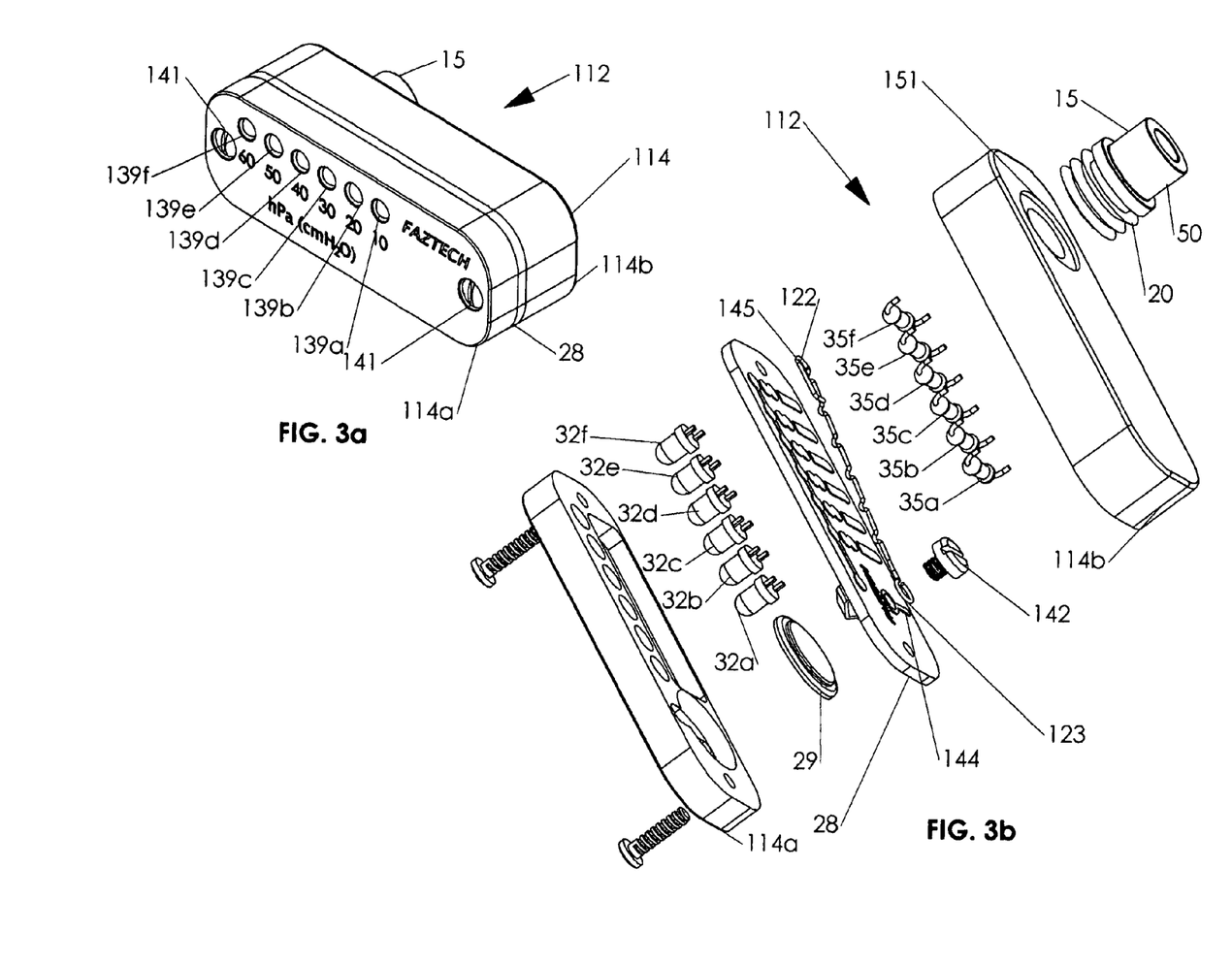
Figure 3C:
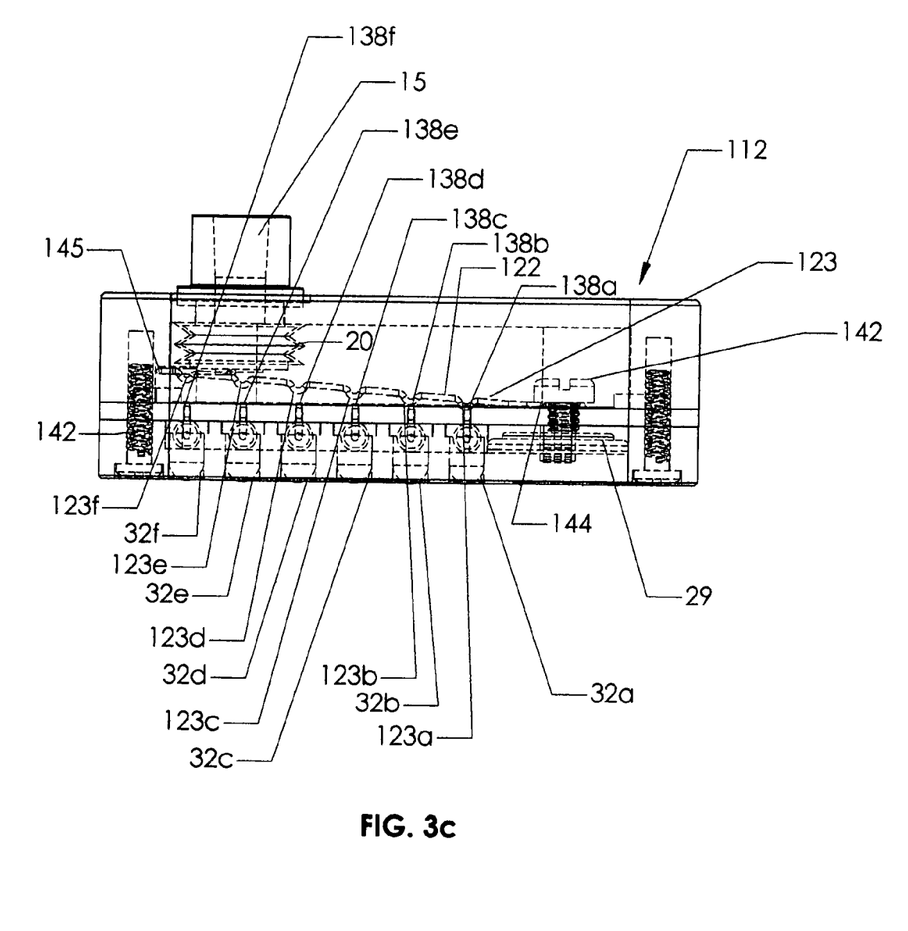

When the sound emitting device 33 is in a first position (as shown in FIGS. 2 and 3), the sound emitting device 33 corresponds to the position of the first light emitting diode 32a, and thus, is electrically connectable with the battery 29 via the spring 23 in the second position. When in a second position, the sound emitting device 33 is electrically connectable with the battery 29 via the spring 23 in the third position. When the sound emitting device 33 is a third, forth, fifth and sixth positions, the sound emitting device 33 is electrically connectable with the battery 29 via the spring 23 in the fourth, fifth, sixth and seventh positions, respectively. It should be appreciated that because the spring 23 cumulatively connects the pressure indicators 31a–g to the battery 29, the sound emitting device 33 will remain connected to the battery 29 as the pressure chamber 20 expands to positions beyond the predetermined position at which the sound emitting device 33 would initially connected to the battery 29.

Referring to FIG. 2c, there is shown an isometric view of the pressure gauge 12. Each light emitting diode 32a–f is positioned adjacent to the corresponding pressure value and partially positioned outside of the apparatus housing 14. Although the first-sixth light emitting diodes 32a–f correspond to 10–60 hPa, it should be appreciated that the pressure gauge of the present disclosure can be designed so the light emitting diodes correspond to various pressures. It should also be appreciated that the light emitting diodes could illuminate any color. In fact, each light emitting diode could illuminate a different color. The sound emitting device 33 is coupled to move with a controller, illustrated as a lever 37, that is positioned outside of the housing 14. When the technician moves the lever 37, the sound emitting device 33, along with the exposed lead connected to the sound emitting device 33, slides along a groove defined by the gauge housing 14 in a conventional manner. The lever 37 can be moved between the six positions, each position being aligned with a different light emitting diode 32a–f. The gauge housing 14 includes a first and second portions 14a and 14b that are removeably attached to one another. Preferably, the first and second portions 14a and 14b can be separated such that the expandable pressure chamber 20 can be removed and replaced. Thus, the expandable pressure chamber 20 is removeably attached to the housing 14.

Referring to FIG. 3a, there is shown an isometric view of a pressure gauge 112, according to a first alternative embodiment of the present disclosure. A gauge housing 114 of the pressure gauge 112 includes a first and a second portion 114a and 114b attached to one another via bolts (shown in FIG. 3b) extending through bores 141. The electric circuit board 28 is positioned between the first and second portions 114a and 114b. Thus, the portions 114a and 114b can be detached from one another in order to allow service of the internal structure, including, but not limited to, replacing the expandable chamber 20. Unlike the pressure gauge 12 in which the light emitting diodes 32a–f are partially positioned outside of the housing 14, the light emitting diodes 32a–f of the pressure gauge 112 are positioned within the housing 114, but illuminate windows 139 defined by the housing 114 and that correspond with various pressures. Pressure values corresponding to each window 139a–f are preferably positioned adjacent to each window 139a–f. Although pressures ranging from 10–60 hPa are illustrated in FIG. 3a, it should be appreciated that the pressure gauge could be designed for various pressures. For instance, by increasing the tension of the spring or by increasing the distance to the electrical circuits, more pressure will be required to move the pressure chamber to the predetermined positions. Although the shape of the pressure gauge 12 varies among embodiments, the pressure gauge 12 is preferably relatively small, being approximately one inch in length and one half inch in width.

Referring to FIG. 3b, there is shown an exploded view of the pressure gauge 112. The second portion 114b of the housing 114 defines a fluid inlet bore 151 in which the fluid inlet port 15 of the expandable pressure chamber 20 is partially positioned. At least a portion of the fluid inlet port 15 extends outside of the housing 114 and acts as the attachment portion 50. The pressure gauge 112 is generally disposable and can be disassembled so that the pressure chamber 20 can be removed and replaced with ease. Similar to the pressure gauge 12, the pressure gauge 112 includes six parallel electric circuits sharing the battery 29. Each electric circuit includes one of the light emitting diodes 32a–f and a resister 35a–f. Similar to pressure gauge 12, there is an electrical conductor 122 attached, at a first end 144, to the circuit board 28 and electrically connected to the battery 29. The electric circuits are position such that the electrical conductor 122 that is coupled to move with the expandable pressure chamber 20 will cumulatively close each electrical circuit as the expandable pressure chamber 20 expands through the plurality of predetermined positions. Whereas the electrical conductor 22 includes a coil-band spring 23, the electrical conductor 122 includes a leaf spring 123. The first end 144 of the leaf spring 123 is attached to circuit board 28 via a screw 142 that also electrically connects the spring 123 to the battery 29, and a second end 145 is coupled to move with the pressure chamber 20.

Referring to FIG. 3c, there is shown a side diagrammatic representation of the internal structure of the pressure gauge 112. When the expandable pressure chamber 20 is in the second predetermined position (as shown in FIG. 3c) and the leaf spring 123 is in a second position, a first portion 123a of the leaf spring 123 is in contact with the lead 138a within the first electric circuit 30a, thereby connecting the battery 29 to the first light emitting diode 32a. As the expandable pressure chamber 20 expands, the leaf spring 123 will move through a second, third, forth, fifth and sixth positions, thereby cumulatively connecting the battery 29 to the second, third, fourth, fifth and sixth light emitting diodes 32b–f via the second, third, fourth, fifth and sixth portions 123a–f, respectively. Although not shown with a sound emitting device, it should be appreciated that the pressure gauge 112 could include a sound emitting device that operates similarly to the sound emitting device 33 of pressure gauge 12.

Figure 4A:
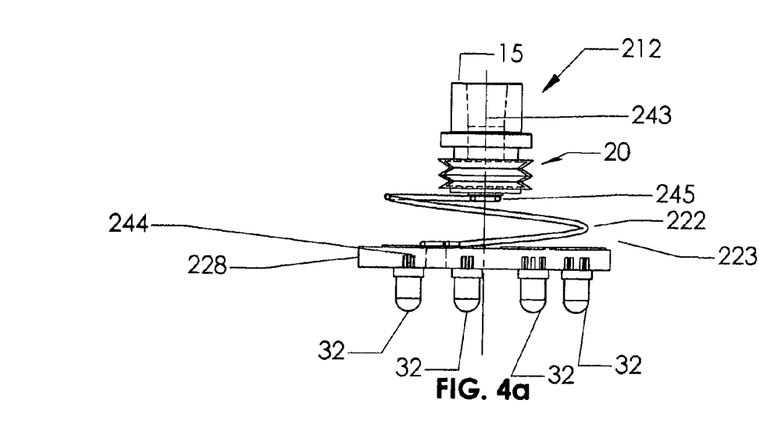
FIG. 4a is a side diagrammatic view of an internal structure of a pressure gauge, according to a second alternative embodiment of the present disclosure.

Referring to FIG. 4a, there is shown a side diagrammatic representation of an internal structure of a pressure gauge 212, according to a second alternative version of the present disclosure. Similar to pressure gauges 12 and 112, pressure gauge 212 includes the expandable pressure chamber 20 fluidly connected to the fluid cavity 13 of the CPR bag assembly 10. The electrical conductor 222 is coupled to move with the expandable pressure chamber 20 and with respect to the gauge body (not shown). Whereas the electrical conductors 22 and 122 include the coil-band spring 23 and the leaf spring 123, respectively, the electrical conductor 222 includes a spiral spring 223. A first end 244 of the spiral spring 223 is secured to a circuit board 228 and a second end 245 is attached to the expandable pressure chamber 20 that is positioned along a center line 243 of the circuit board 228. Although the ends 244 and 245 are illustrated as including hooks that can be attached to protrusions on the circuit board 228 and pressure chamber 20, respectively, it should be appreciated that the spring 223 can be attached in various manners. Those skilled in the art will appreciate that the battery (not shown) can be included within the pressure gauge 212 at various locations and electrically connected to the spiral spring 223 in any conventional manner.

Figure 4B:
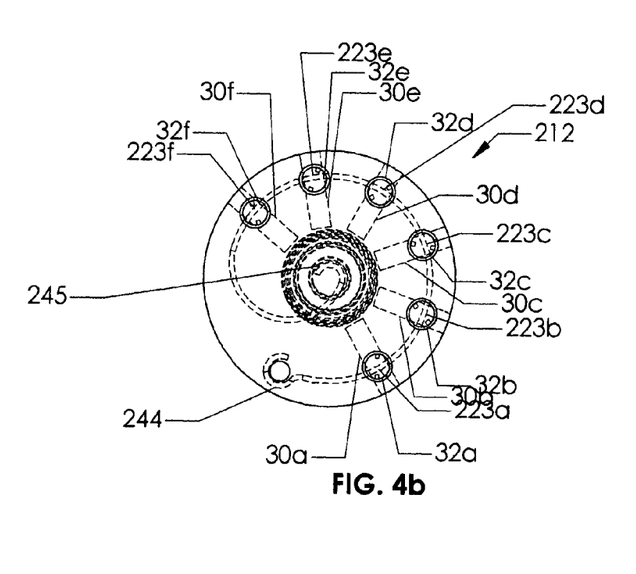

Referring to FIG. 4b, there is shown a bottom diagrammatic representation of the internal structure of the pressure gauge 212. As the expandable pressure chamber 20, and thus the spiral spring 223, move through the plurality of positions along the center line 243, the spiral spring 223 will cumulatively electrically connect each light emitting diodes 32a–f to the battery 29. When the expandable pressure chamber 20 and the spiral spring 223 are in a first position, the spiral spring 223 is out of contact with all the electric circuits 31a–f, and thus, the battery 27 is not electrically connected to any of the light emitting diodes 32a–f. When the expandable pressure chamber 20 and the spiral spring 223 are in a second position, a first portion 233a of the spiral spring 223 is in contact with the first electric circuit 30a, thereby electrically connecting the battery 29 to the first light emitting diode 32a. As the expandable pressure chamber 20 expands through a third, fourth, fifth, sixth, and seventh predetermined positions, the spiral spring 223 will advance, thereby connecting the battery 29 to the second, third, fourth, fifth and sixth light emitting diodes 32b–f, respectively via a second, third, fourth, fifth and sixth portions 223b–f of the spiral spring 223. Although each electrical circuit 30a–f is illustrated by the dotted lines, it should be appreciated that the leads for each electric circuit 30a–f that come in contact with the spiral spring 233 are not shown in FIG. 4b.

Figure 5:
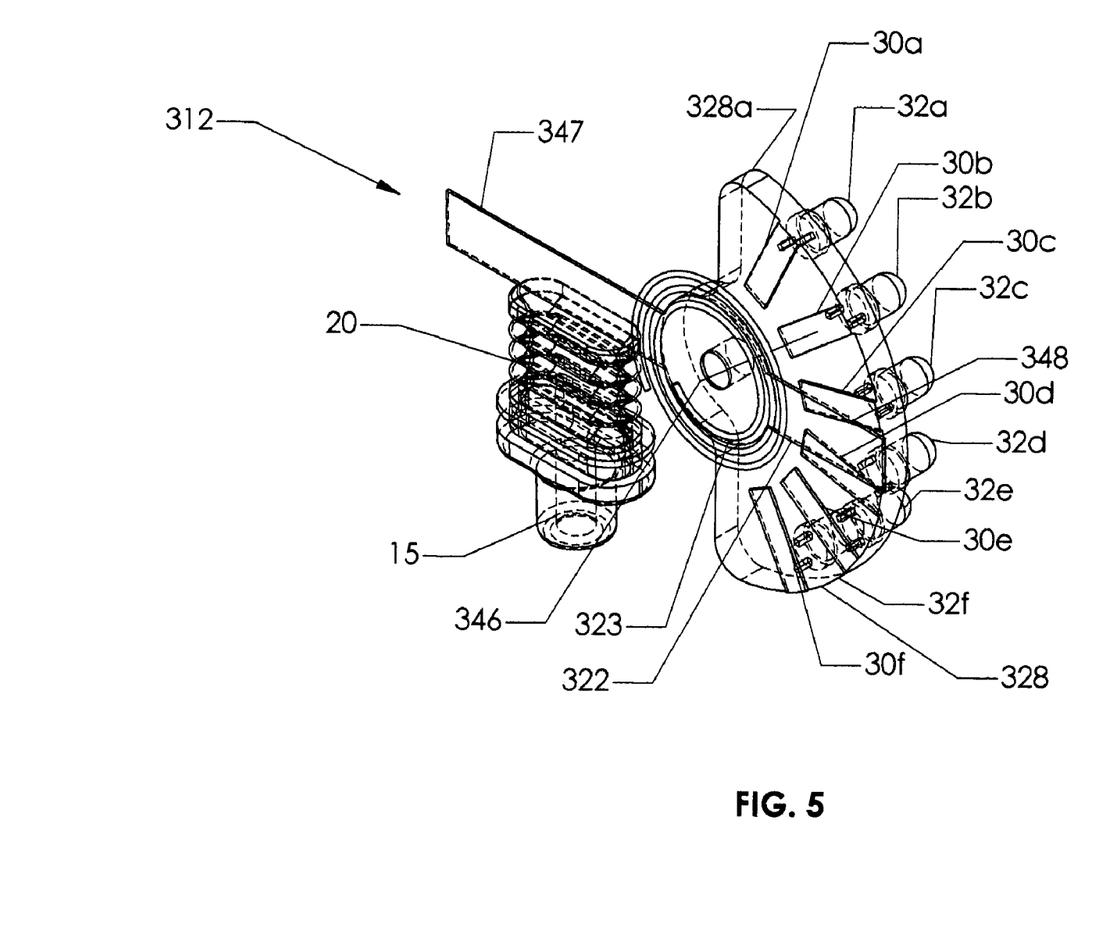
FIG. 5 is a diagrammatic view of an internal structure of a pressure gauge, according to a third embodiment of the present disclosure.

Referring to FIG. 5, there is shown an internal structure of a pressure gauge 312, according to a third alternative embodiment of the present disclosure. The pressure gauge 312 is similar to the pressure gauges 12, 112 and 212 in that the pressure gauge 312 includes the expandable pressure chamber 20 fluidly connected to the fluid cavity 13 (shown in FIG. 1b) via the fluid inlet port 15. An electric conductor 322 is coupled to move with the expandable pressure chamber 20 among a plurality of positions. As the conductor 322 moves through the positions, the conductor 322 electrically connects a plurality of light emitting diodes 32a–f to the battery 29. However, unlike the electrical conductors 22, 122 and 222 that cumulatively connect each light emitting diode 32a–f to the battery 29, the conductor 322 singularly electrically connects each light emitting diode 32a–f to the battery 29. The electrical conductor 322 includes a torsion spring 323 coiled around a spring holder and to which a conductive connector 348 is attached. The spring 323 is in electrical communication with the battery (not shown) that can be positioned at various locations. For instance, the battery could be positioned along a center axis 346 of the spring 323. It should be appreciated that the connector 348 could be made, at least in part, from any type of conductive material and can be of any shape as long as the connector 348 can contact each electrical circuit 32a–f when the expandable pressure chamber 20 is at the corresponding predetermined position. The pressure chamber 20 is coupled to the torsion spring 323 by a coupler 347 attached to an opposite side of the spring 323 than the connector 348. The coupler 347 can be any component that can transfer the transverse motion of the expandable pressure chamber 20 to the rotary motion of the torsion spring 323. The coupler 347 need not include a conductive material.

When the expandable pressure chamber 20 is in a first predetermined position, the spring 323 and connector 348 will be in a first position in which the connector 348 will be out of contact with all of the electric circuits 30a–f. The connector 348 will be positioned at a top 328a of the circuit board 328. When the pressure chamber 20 expands to a second predetermined position, the spring 323 and the connector 348 will move to a second position in which the connector 348 is in contact with the first electric circuit 30a, thereby connecting the first light emitting diode 32a to the battery 29. When the pressure chamber 28 expands to a third predetermined position, the spring 323 and the connector 348 will move to a third position in which the connector 348 is out of contact with the first circuit 30a and in contact with the second electric circuit 30b, thereby disconnecting the first light emitting diode 32a from the battery 29 and connecting the second light emitting diode 32b to the battery 29. As the pressure chamber 20 and the connector 348 move through the fourth, fifth, sixth and seventh positions, the light emitting diodes 32c–e will be connected and disconnected to the battery 29 in a similar manner as was the first and second light emitting diodes 32a and 32b. It should be appreciated that the pressure gauge 312 could be designed to cumulatively connect the battery to each light emitting diode. For instance, the connector could be sickle shaped. As the connector advances through the positions, the sickle portion of the connector would continue to contact the previous circuits. It should also be appreciated that the exposed lead within each circuit 30a–f is not illustrated.

Figure 6:
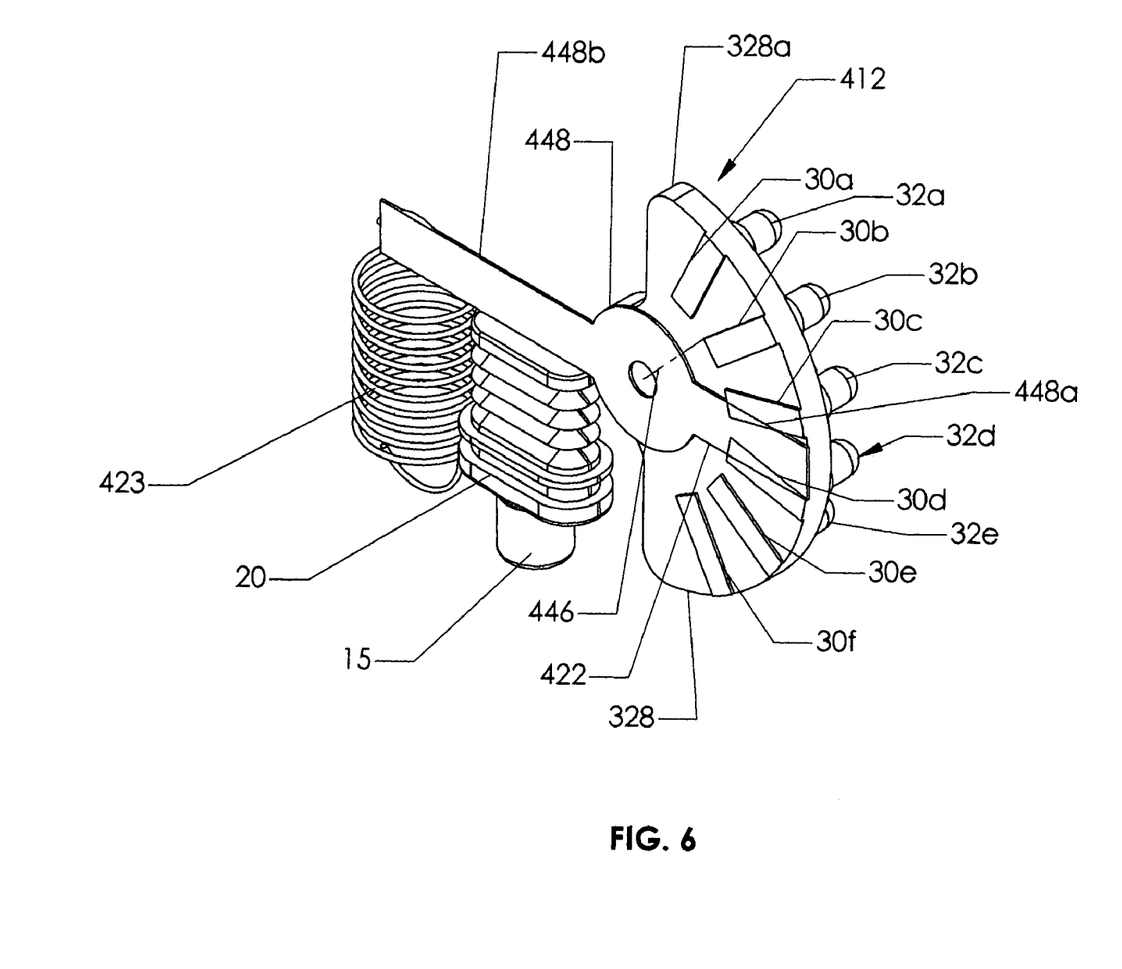
FIG. 6 is a diagrammatic view of an internal structure of a pressure gauge, according to a fourth embodiment of the present disclosure.

Referring to FIG. 6, there is shown an angled diagrammatic representation of an internal structure of a pressure gauge 412, according to a third alternative embodiment of the present disclosure. The pressure gauge 412 is similar to pressure gauge 312 except that the electrical conductor 422 includes a connector 448 that is coupled to an extension spring 423 rather than the torsion spring 323. The connector 448 is separated into a contact portion 448a and a lever portion 448b that are attached to opposite sides of a circular center piece that is rotatably attached to a circuit board 328 about a center axis 446 of the center piece. The lever portion 448b makes contact with the expandable pressure chamber 20 and the contact portion 448a contacts the electrical circuits 30a–f. The extension spring 423 is attached, at one end, to the lever portion 448b of the connector 448 and, at the other end, to the gauge housing (not shown). The connector 448 is in electrical communication with the battery (not shown) via the spring 423. Although the expandable pressure chamber 20 is shown positioned between the extension spring 423 and the center piece, it should be appreciated that the spring could be positioned between the pressure chamber 20 and the center piece as long as both the spring and the pressure chamber are coupled to the lever portion 448a. The pressure within the pressure chamber 20 required to rotate the connector 448 may differ depending on the coupling location of the pressure chamber 20 to the connector 448.

Figure 7:
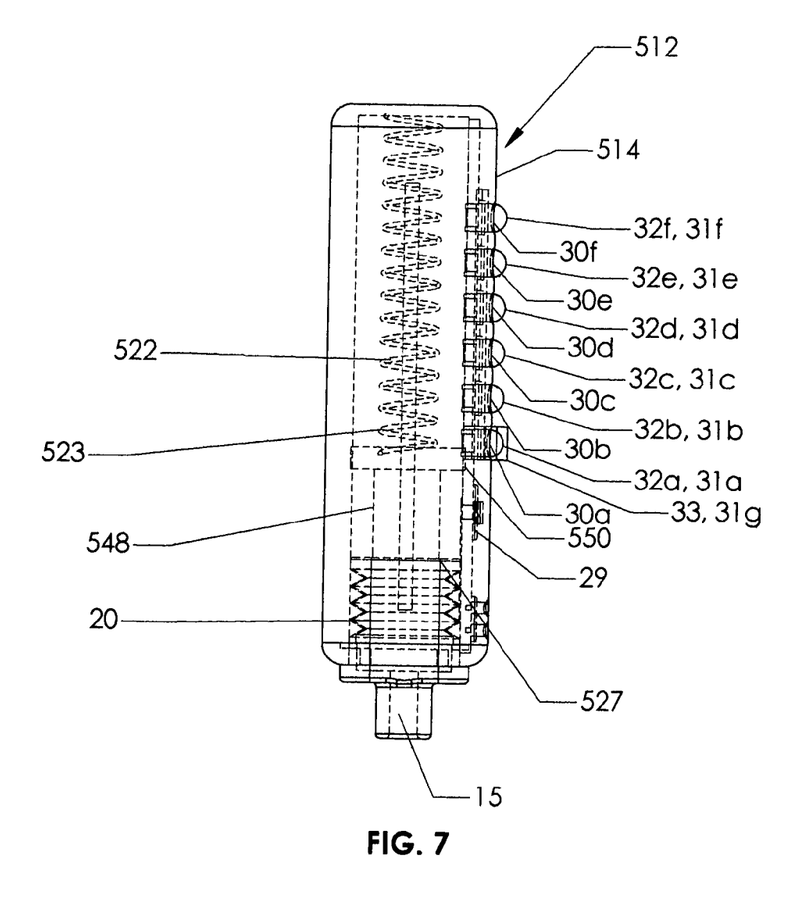
FIG. 7 is a top diagrammatic view of an internal structure of a pressure gauge, according to a forth alternative embodiment of the present disclosure.

Referring to FIG. 7, there is shown a top diagrammatic representation of an internal structure of a pressure gauge 512, according to a fourth embodiment of the present disclosure. Pressure gauge 512 includes a gauge body 514 similar to the gauge body 14 of the pressure gauge 12. The pressure gauge 512 also preferably includes six light emitting diodes 32a–f arranged sequentially in a line and the adjustable sound emitting device 33 coupled to the lever 37. The pressure gauge 512 includes the expandable pressure chamber 20 with the fluid inlet port 15 that is connected to the fluid cavity 13 (shown in FIG. 1b). However, unlike the pressure gauge 12, an electrical conductor 522 includes a compression spring 523 coupled to a sliding connector 548. The spring 52 is coupled to move with the pressure chamber 20 via the sliding connector 548 that is illustrated as a cylindrical electrically conductive component positioned between the chamber 20 and the spring 523. The connector 548 includes a chamber contact surface 527 and a circuit contact surface 550 and is in electrical communication with the battery 29 via the spring 523.

When the spring 523 and connector 548 are in a first position, the connector 548 is out of contact with all of the electric circuits 30a–f. When the pressure chamber 20 expands to a second predetermined position, the connector 548 moves against the bias of the spring 523 to a second position in which the circuit contact surface 550 contacts the first electric circuit 30a, thereby electrically connecting the battery 29 with the first light emitting diode 32a and the sound emitting device 33. When the pressure chamber 20 expands to a third predetermined position, the connector 548 moves against the bias of the spring 523 to a third position in which the circuit contact surface 550 contacts the second electric circuit 30b and moves out of contact with the first electric circuit 30a, thereby electrically connecting the battery 29 to the second light emitting diode 32b and disconnecting the battery 29 from the first light emitting diode 32a and the sound emitting device 33. As the pressure chamber 20 expands, the connector 548 will moves through a third, fourth, fifth and sixth positions, thereby connecting and disconnecting the battery 29 with the third, fourth, fifth and sixth light emitting diodes 32c–f similar to light emitting diodes 32a and b. Those skilled in the art will appreciate that the pressure gauge 512 could be modified such that the conductor 522 cumulatively connects the battery 29 to the pressure indicators 31a–g. For instance, the length of the circuit contact surface 550 could increased such that at least more than one circuit is contacted at one time.

INDUSTRIAL APPLICABILITY

Referring to FIGS. 1a–7, a method of indicating pressure within the fluid cavity 13 of the CPR bag assembly 10 will be discussed. Although the method will be discussed for the CPR bag assembly 10, it should be appreciated that the present disclosure will operate similarly any type of CPR bag assembly or medical apparatus designed to deliver fluid, being liquid or air, to and from a patient. Further, the present disclosure could be applied to non-medical apparatuses in which the pressure of the fluid within a chamber must be monitored and indicated regardless of whether the fluid will be delivered to a person. Although the present disclosure will be discussed for the pressure gauge 12 of the preferred embodiment, it should be appreciated that the pressure gauges 112, 212, 312, 412, and 512 generally operate similarly. Any differences will be noted within the discussion.

Referring specifically to FIGS. 1a–b, the expandable pressure chamber 20 is expanded with the air pressure from the fluid cavity 13 by fluidly connecting the fluid cavity 13 with the fluid inlet port 15 of the expandable pressure chamber 20. When the technician releases the squeeze bulb 16, oxygen will be drawn into the bulb 16 from the reservoir bag 18 via the inlet port 19. When the technician squeezes the squeeze bulb 16, the oxygen within the bulb 16 will be pushed out the outlet check valve of the bulb 16 to the fluid cavity 13 of the outlet assembly 17. When the pressure of the oxygen reaches a threshold pressure, the outlet valve within the outlet assembly 17 will open and the oxygen will flow, via the outlet 34, to the mask over the patient's mouth and nose. As the oxygen flows through the fluid cavity 13, the oxygen will flow into the fluid inlet port 15 defined by the gauge body 14. The pressure of the oxygen flowing into the expandable pressure chamber 20 will push against the bellow-type wall 21 and expand the pressure chamber 20. The greater the pressure, the more the pressure chamber 20 will expand.

Referring specifically to FIGS. 2a–c, the electrical conductor 22 is coupled to move with the expandable pressure chamber 20. According to the preferred embodiment, the electrical conductor 22 includes the coil-band spring 23 coupled to the spring slide assembly 24. The expanding pressure chamber 20 will contact the contact surface 27 of the spring slide 26, causing the holder to slide along the gauge housing 14. Because the coil-band spring 23 coiled around the spring holder 25 attached the spring slide 26 is attached, at the first end 44, to the circuit board 28, the coil-band spring 23 will uncoil as the spring slide assembly 24 moves along the spring path.

The electrical conductor 22, being the coil-band spring 23 coupled to the spring slide assembly 24, will electrically connect the battery 29 with the plurality of pressure indicators 31a–g as the pressure chamber 20 expands through the plurality of predetermined positions. Although the pressure indicators 31a–g include the light emitting diodes 32a–f and the sound emitting device 33, the present disclosure contemplates various types of pressure indicators. For instance, all embodiments could include any number of light emitting diodes and may or may not include the sound emitting device. Each of the predetermined positions of the pressure chamber 20 corresponds to a predetermined pressure that is indicated on the gauge housing 14 adjacent each light emitted diode 32a–f (illustrated in FIG. 2c). When the pressure within the expandable chamber 20 is below 10 hPa (as illustrated in FIG. 2c), the expandable pressure chamber 20 will be in the first predetermined position, causing the coil-band spring 23 to also be in the first position. The spring 23 will be out of contact with all of the electrical circuits 30a–g (as shown in FIGS. 2a and 2b) and none of the pressure indicators 31a–g are connected to the battery 29. Thus, the technician can determine from the pressure indicator 12 with no light emitting diodes 32a–f illuminated or without the sound emitting device 33 making noise that the pressure of the oxygen being delivered to the patient is below 10 hPA.

When the air pressure within the expandable chamber 20 increases to 10 hPa, the expandable chamber 20 will expand to the second predetermined position, causing the coil-band spring 23 to move to the second position. In the second position, the first portion of the coil-band spring 23 contacts the first electrical circuit 30a, causing the light emitting diode 32a to be electrically connected to the battery 29 and illuminate. The illuminated light emitting diode 32a can quickly indicate to the technician that the pressure of the air being delivered to the patient is 10 hPa.

As illustrated in FIGS. 2a–c, the sound emitting device 33 has been adjusted to connect with the battery 29 when the spring 23 is in the second position. Thus, the sound emitting device 33 is positioned such that the device 33 will sound when there is 10 hPa of air pressure in the chamber 20. The technician can adjust the position of the sound emitting device 33 by adjusting the lever 37 to which the exposed lead of the device 33 is coupled. The sound emitting device 33 can be adjusted to connect to the battery 29 when the expandable pressure chamber 20 is at any of the predetermined positions. For instance, if the technician would like the sound emitting device 33 to sound when the pressure reaches 60 hPa, the lever 37 is aligned with the sixth electrical circuit 30f. When the pressure within the pressure chamber 20 is approximately 60 hPa, the chamber 20 will expand to the seventh predetermined position, causing the spring 23 to contact the sixth and seventh electric circuits 30f and g. The sixth light emitting diode 32g is illuminated and the sound emitting device 33 is sounded. Thus, the adjustable sound emitting device 33 allows the technician to concentrate on resuscitating the patient rather than observing the pressure gauge 12 in stressful emergency situations. Moreover, the sound emitting device 33 can be adjusted based on the specific characteristics of a patient. For instance, a technician reviving a frail, older patient may want the sound emitting device 33 to sound at a lower pressure than if the patient were younger and/or stronger.

The coil-band spring 23 cumulatively electrically connects the plurality of light emitting diodes 32a–f to the battery 29. When the pressure within the fluid cavity 13 and thus the expandable pressure chamber 20 rises to 20 hPa, the pressure chamber 20 will expand to the third predetermined position, causing the coil-band spring 23 to contact the second electrical circuit 30b and illuminate the second light emitting diode 32b. Because the coil-band spring 23 stays in contact with the first electrical circuit 30a, both the first and second light emitting diodes 32a and 32b are illuminated. Similarly, as the pressure within the fluid cavity 13 of the CPR bag assembly 10, and thus, the pressure chamber 20 increases from 20 to 60 hPa, the coil-band spring 23 will cumulatively connect electrical circuits 30c–f and illuminate the third, fourth, fifth and sixth light emitting diodes 32c–f. It should be appreciated that as the pressure decreases within the fluid cavity 13, the pressure will decrease within the expandable pressure chamber 20, causing the slide assembly 24 to reverse direction and the coil-band spring 23 to begin to recoil.

Referring specifically to FIGS. 3a–c, the light emitting diodes 32a–f can be cumulatively electrically connected to the battery 29 by various types of springs other than the coil-band spring 23. According to the first alternative embodiment, as the pressure within the fluid cavity 13 of the CPR bag assembly 10, and thus, the expanding pressure chamber 20, increases, the pressure chamber 20 will move against the unattached end of the leaf spring 123, causing the leaf spring 123 to move towards the circuit board 28. The first portion 123a of the leaf spring 123 will contact the first electric circuit 30a, illuminating the first light emitting diode 32a, when the pressure chamber 20 has expanded to the second predetermined position corresponding to the 10 hPa. Similarly, as the pressure within the fluid cavity 13 and pressure chamber 20 increases to 20, 30, 40, 50 and 60 hPa, the pressure chamber 20 will expand to the third, fourth, fifth, sixth and seventh predetermined positions, respectively. When the pressure increases to 60 hPa, the chamber 20 will be at the seventh predetermined position and all of the light emitting diodes 32a–g will be illuminated. It should be appreciated that as the pressure decreases within the fluid cavity 13, the pressure will decrease within the expandable pressure chamber 20, causing the leaf spring 123 to moved toward its biased position and out of contact with the electrical circuits 30a–f.

Referring specifically to FIGS. 4a and 4b, according to the second alternative embodiment, the spiral spring 223 cumulatively connects the battery 29 to the light emitting diodes 32a–f. When the pressure within the expandable chamber 20 increases to 10 hPa, the pressure chamber will move to the second predetermined position, compressing the spring 223 and causing the first portion 223a of the spring 223 to contact the first electric circuit 30a and illuminate the first light emitting diode 32a. As the pressure within the expandable chamber 20 increases to 60 hPa, the pressure chamber will expand through the third, fourth, fifth, sixth and seventh predetermined positions corresponding with 20 hPa, 30 hPa, 40 hPa, 50 hPa and 60 hPa, respectively. The spiral spring 223 will continue to compress, thereby contacting the electrical circuits 30b–f and illuminating light emitting diodes 32b–f. When the pressure reaches 60 hPa, the chamber 20 will be at the seventh predetermined position, and all of the light emitting diodes 32a–f will be connected to the battery 29 and be illuminated. It should be appreciated that as the pressure decreases within the CPR bag 18, the pressure will decrease within the expandable pressure chamber 20, causing the spiral spring 223 to move toward its biased position, and out of contact with the electrical circuits 30a–f Referring specifically to FIG. 5, the light emitting diodes 32a–f can be connected to the battery 29 via the electrical conductor 322 including the connector 348 and the coupler 347 attached to the torsion spring 523. The connector 348, not the spring 323, contacts the electrical circuits 30a–f as the expandable pressure chamber 20 expands through the plurality of predetermined pressures. For instance, the pressure chamber 20 is illustrated as being in the fifth predetermined position, corresponding to 40 hPa within the pressure chamber 20 and the fluid cavity 13. The force of the expanding pressure chamber 20 moves the coupler 347 which rotates the spring 323 and the connector 348. When the pressure is 40 hPa, the connector 348 makes contact with the fourth electric circuit 30d, thereby illuminating the fourth light emitting diode 32d. Preferably, the connector 348 is sufficiently wide that, as the pressure chamber 20, and thus connector 348, are moving between positions, the connector 348 can briefly contact two adjacent electric circuits simultaneously. Thus, when the pressure is over 10 hPa, there will always be at least one light emitting diode 32a–f illuminated to indicate the pressure to the technician. However, it should be appreciated that the present disclosure contemplates a pressure gauge where there is a brief transition pause where no light emitting diodes are illuminated as the connector moves between positions. Further, the present disclosure contemplates the connector being shaped such that any number of adjacent light emitting diodes can be cumulatively illuminated. It should be appreciated that as the pressure decreases within the fluid cavity 13, the pressure will decrease within the expandable pressure chamber 20, causing the torsion spring 323 to move toward its biased position, and the connector 348 to move back towards the first position.

Referring to FIG. 6, the light emitting diodes 32a–f are electrically connected to the battery 29 via the electrical conductor 422 that includes the connector 448 coupled to the extension spring 423. Similar to the connector 348, connector 448 moves through the plurality of positions such that, at least, one light emitting diode 32a–f is illuminated when the pressure within the fluid cavity 13, and thus the expandable pressure chamber 20, is above 10 hPa. However, rather than the connector 348 being coupled to the torsion spring 323 (as shown in FIG. 5), the lever portion 448b of the connector 448 is coupled to the extension spring 423. It should be appreciated that as the pressure decreases within the fluid cavity 13, the pressure will decrease within the expandable pressure chamber 20, causing the extension spring 423, and thus, the connector 448, to move toward its biased position.

Although the pressure gauge 12, 112, 212, 312, 412 and 512 of each embodiment is illustrated as including a spring 23, 123, 223, 323, 423 and 523 within the electrical conductor 22, 122, 222, 322, 422 and 522, those skilled in the art should appreciate that the electrical conductor need not include a spring. The electrical conductor can include any component that is electrically conductive and coupled to move with the expandable pressure chamber.

The present disclosure is advantageous because the pressure gauge 12 indicates the fluid pressure to the technician through an easy-to-read display and a sound emitting device 33. The pressure gauge 12 is often used in emergency situations in which the patient is being resuscitated. Because the pressure gauge 12 indicates the pressure by illuminating sequentially arranged light emitting diodes 32a–f, the technician can determine the pressure of the oxygen within the fluid cavity 13 being supplied to the patient by glancing at the pressure gauge 12. Because the technician is not spending a significant amount of time monitoring the pressure gauge 12 to determine if the pressure becomes too high, the technician can focus his attention on the patient who is being resuscitated. In emergency medical situations, any saved time can save lives.

The pressure gauge 12 is even further advantageous because the pressure gauge 12 includes an added assurance that the specific patient is being supplied air properly. It is known that some patients can handle more pressure within their lungs than other patients. For instance, a small child or an elderly individual cannot tolerate as much pressure than can a middle-aged adult. Thus, the technician can set the adjustable sound emitting device 33 to the pressure threshold for the specific patient. Even if the technician is not observing the pressure gauge 12, the device 33 can indicate to the technician that the pressure is too high. Again, the technician can concentrate on resuscitating the patient rather than constantly monitoring the pressure. Moreover, the pressure gauge 12 helps assure that the patient is not further harmed during resuscitation.

Further, the pressure gauge 12 is advantageous because the gauge is relatively inexpensive, small, and partially disposable. The pressure gauge 12 includes relatively few inexpensive components that are coupled to one another to indicate the pressure within the fluid cavity 13 of the CPR bag assembly 10. Although the present disclosure was designed to indicate pressures between 10 hPa and 60 hPa, the pressure gauge 12 can be designed to indicate various sequential pressures. For instance, in order to indicate pressures greater than 60 hPa, the length and the tension of the spring 23 can be increased. Although the housing for each embodiment is of a different shape, the housings can be easily disassembled so that the internal structure of the pressure gauge can be serviced. As part of the service, the pressure chamber 20 can be removed from the housing 14 and replaced. Further, each pressure gauge 12, 112, 212, 312, 412 and 512 is relatively small, about one inch in length, and does not interfere with the work of the technician. Because the pressure gauge 12 attached to the fluid cavity 13 is a closed system, leakage of the air does not affect the pressure readings. Although the present disclosure has been described for use with a medical apparatus, it should be appreciated that the pressure gauge 12 could be used with various other medical and non-medical apparatus.

It should be understood that the above description is intended for illustrative purposes only, and is not intended to limit the scope of the present invention in any way. Thus, those skilled in the art will appreciate that other aspects, objects, and advantages of the invention can be obtained from a study of the drawings, the disclosure and the appended claims.

The invention claimed is:

1. A pressure gauge comprising:
   a gauge body;
   an expandable pressure chamber being at least partially positioned within the gauge body and including a fluid inlet port;
   at least one electrically actuated pressure indicator being at least partially positioned within the gauge body;
   at least one battery being at least partially positioned within the gauge body;
   an electrical conductor being moveable with the expandable pressure chamber and with respect to the gauge body and including a plurality of positions; and
   when the electrical conductor is in a first position, the battery being out of electrical connection with the at least one pressure indicator, and when in a second position, the electrical conductor electrically connects the battery with the at least one pressure indicator.

2. The pressure gauge of claim 1 wherein the electrical conductor includes an electrically conductive spring.

3. The pressure gauge of claim 2 wherein the spring includes a leaf spring including a first end coupled to the expandable pressure chamber and a second end connected to the battery and secured to a gauge component including at least one electric circuits, connected to the at least one pressure indicator; and
   when the leaf spring is in the first position, the leaf spring is out of contact with the at least one electrical circuit, and when the leaf spring is in the second position, a first portion of the leaf spring is in contact with the at least one electrical circuit.

4. The pressure gauge of claim 2 wherein the spring includes a coil-band spring with a first end connected to the battery and attached to a gauge component including at least one electric circuit and being coiled around a spring slide assembly coupled to move with the expandable pressure chamber; and
   when the coil-band spring is in the first position, the coil-band spring is out of contact with the at least one electrical circuit, and when the coil-band spring is in the second position, a first portion of the coil-band spring is in contact with the at least one electrical circuit.

5. The pressure gauge of claim 1 wherein the at least one pressure indicator being a sound emitting device.

6. The pressure gauge of claim 1 wherein the at least one pressure indicator being a first light emitting diode within a plurality of light emitting diodes; and
   the plurality of light emitting diodes including a third, fourth, fifth and sixth light emitting diodes.

7. The pressure gauge of claim 6 wherein the electrical conductor includes a third, fourth, fifth, sixth and seventh positions; and
   when in the third position, the electrical conductor electrically connects the battery with the first and second light emitting diodes; when in the fourth position, the electrical conductor electrically connects the battery with the first, second and a third light emitting diodes; when in the fifth position, the electrical conductor electrically connects the battery with the first, second, third and a fourth light emitting diodes; when in the sixth position, the electrical conductor electrically connects the battery with the first, second, third, fourth and a fifth light emitting diodes; and when in the seventh position, the electrical conductor electrically connects the first, second, third, fourth, fifth and a sixth light emitting diodes.

8. The pressure gauge of claim 7 wherein the plurality of pressure indicators includes a sound emitting device being adjustable between a plurality of positions; and
   when the sound emitting device is in a first position, the sound emitting device is electrically connectable with the battery via the electrical conductor in the second position; and when the sound emitting device is in a second position, the sound emitting device is electrically connectable with the battery via the electrical conductor in the third position; when the sound emitting device is in a third position, the sound emitting device is electrically connectable with the battery via the electrical conductor in the fourth position; when the sound emitting device is in a fourth position, the sound emitting device is electrically connectable with the battery via the electrical conductor in the fifth position; when the sound emitting device is in a fifth position, the sound emitting device is electrically connectable with the battery via the electrical conductor in the sixth position.

9. The pressure gauge of claim 8 wherein the electrical conductor includes an electrically conductive spring; and
   the expandable pressure chamber being removeably attached to the gauge body.

10. A medical apparatus comprising:
    an apparatus body defining a fluid cavity; and
    a pressure gauge including a gauge body; an expandable pressure chamber being at least partially positioned within the gauge body and including a fluid inlet port being in fluid communication with the fluid cavity; at least one battery and at least one electrically actuated pressure indicator being at least partially positioned within the gauge body; an electrical conductor being moveable with the expandable pressure chamber and with respect to the gauge body and including a plurality of positions; and when the electrical conductor is in a first position, the battery being out of electrical connection with the at least one pressure indicator; when in a second position, the electrical conductor electrically connects the battery with the at least one pressure indicator.

11. The medial apparatus of claim 10 wherein the at least one pressure indicator being a first pressure indicator within a plurality of pressure indicators; and
    when in a third position, the electrical conductor electrically connects the battery with at least a second pressure indicator.

12. The medical apparatus of claim 11 wherein the plurality of pressure indicators includes a first light emitting diode being the first pressure indicator, a second light emitting diode being the second light emitting diode, a third light emitting diode, a fourth light emitting diode, a fifth light emitting diode and a sixth light emitting diode;
    the electrical conductor includes a fourth position, a fifth position, a sixth position and a seventh position; and
    when in the third position, the electrical conductor electrically connects the battery with the first and second light emitting diodes; when in the fourth position, the electrical conductor electrically connects the battery with the first, second and third light emitting diodes;

when in the fifth position, the electrical conductor electrically connects the battery with the first, second, third and fourth light emitting diodes; when in the sixth position, the electrical conductor electrically connects the battery with the first, second, third, fourth and fifth light emitting diodes; and when in the seventh position, the electrical conductor electrically connects the first, second, third, fourth, fifth and sixth light emitting diodes.

13. The medical apparatus of claim 12 wherein the plurality of pressure indicator includes at least one sound emitting device being adjustable among a plurality of positions; and when the sound emitting device is in a first position, the sound emitting device is electrically connectable with the battery via the electrical conductor in the second position; and when the sound emitting device is in a second position, the sound emitting device is electrically connectable with the battery via the electrical conductor in the third position; when the sound emitting device is in a third position, the sound emitting device is electrically connectable with the battery via the electrical conductor in the fourth position; when the sound emitting device is in a fourth position, the sound emitting device is electrically connectable with the battery via the electrical conductor in the fifth position; when the sound emitting device is in a fifth position, the sound emitting device is electrically connectable with the battery via the electrical conductor in the sixth position.

14. The medical apparatus of claim 13 wherein the electrical conductor includes an electrically conductive spring.

15. The medical apparatus of claim 14 wherein the medical apparatus includes a cardiopulmonary resuscitation apparatus.

16. A method of indicating fluid pressure within a fluid cavity, comprising the steps of:

expanding an expandable pressure chamber with the fluid pressure from the fluid cavity, at least in part, by fluidly connecting the fluid cavity with a fluid inlet port of the expandable pressure chamber;

moving an electrical conductor with the expanding pressure chamber; and electrically connecting, via the electrical conductor, a battery with a plurality of pressure indicators when the expandable pressure chamber is at a plurality of corresponding predetermined positions.

17. The method of claim 16 wherein the step of electrically connecting includes a step of adjusting at least one sound emitting device to connect, via the electrical conductor, to the battery when the expandable pressure chamber is at the predetermined position.

18. The method of claim 16 wherein at least one pressure indicator within the plurality of pressure indicators includes a light emitting diode.

19. The method of claim 17 wherein the step of electrically connecting includes a step of sequentially electrically connecting, via the electrical conductor, the battery with a first, second, third, fourth, fifth and sixth light emitting diode when the expandable pressure chamber is at a second, third, fourth, fifth, sixth and seventh predetermined position, respectively.

20. The method of claim 19 wherein the step of electrically connecting includes a step of cumulatively electrically connecting, via the electrical conductor, the plurality of light emitting diodes with the battery as the expandable pressure chamber expands through the plurality of predetermined positions.

* * * * *